United States Patent [19]

Howe et al.

[11] 4,251,261

[45] Feb. 17, 1981

[54] 2-CHLORO-4-TRIFLUOROMETHYL-5-THIAZOLECARBOXYLIC ACIDS AND DERIVATIVES

[75] Inventors: Robert K. Howe, Bridgeton; Len F. Lee, Maryland Heights, both of Mo.

[73] Assignee: Monsanto Company, St. Louis, Mo.

[21] Appl. No.: 27,963

[22] Filed: Apr. 9, 1979

Related U.S. Application Data

[63] Continuation-in-part of Ser. No. 906,183, May 15, 1978, Pat. No. 4,199,506.

[51] Int. Cl.³ .................. A01N 43/78; A01N 37/18
[52] U.S. Cl. ........................................ 71/90; 71/118
[58] Field of Search ................................ 71/90, 118

[56] References Cited

U.S. PATENT DOCUMENTS

| | | | |
|---|---|---|---|
| 3,131,509 | 5/1964 | Hoffman | 71/77 |
| 3,505,055 | 4/1970 | von Schmeling et al. | 71/77 |
| 3,989,503 | 11/1976 | Pallos et al. | 71/90 |
| 4,022,611 | 5/1977 | Vogel et al. | 71/118 |
| 4,115,095 | 9/1978 | Franz et al. | 71/90 |
| 4,144,047 | 3/1979 | Franz et al. | 71/90 |

*Primary Examiner*—Glennon H. Hollrah
*Attorney, Agent, or Firm*—Richard H. Shear; Donald W. Peterson

[57] ABSTRACT

2-Chloro-4-trifluoromethyl-5-thiazolecarboxylic acids and derivatives thereof have been found to reduce herbicidal injury of sorghum plants due to the application thereto of 2-chloro-N-(2-methoxy-1-methylethyl)-6'-ethyl-o-acetotoluidide.

6 Claims, No Drawings

2-CHLORO-4-TRIFLUOROMETHYL-5-THIAZOLECARBOXYLIC ACIDS AND DERIVATIVES

This application is a continuation-in-part of Ser. No. 906,183 filed May 15, 1978, now U.S. Pat. No. 4,199,506.

This invention relates to novel 2-chloro-4-trifluoromethyl-5-thiazolecarboxylic acids and derivatives thereof as well as their use in compositions and methods for reducing herbicidal injury. More specifically, the invention relates to novel compositions and methods for reducing injury to crop plants by herbicides, such as 2-chloro-N-(2-methoxy-1-methylethyl)-6'-ethyl-o-acetotoluidide, which comprises treating the crop plant locus or the seed of the crop plant with an effective amount of a 2-chloro-4-trifluoromethyl-5-thiazolecarboxylic acid or derivative thereof that will be described more fully below.

BACKGROUND OF THE INVENTION

2-Chloro-N-(2-methoxy-1-methylethyl)-6'-ethyl-o-acetotoluidide is also known as 2-ethyl-6-methyl-N-(1'-methoxyprop-2'-yl)-N-chloroacetanilide (hereinafter referred to by its common name metolachlor) and is the active ingredient in Dual ® herbicide manufactured by Ciba-Geigy Corporation. Said compound has the formula

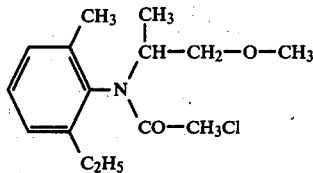

Acetanilide herbicides, such as metolachlor, are useful for controlling certain weeds, especially grasses, in the presence of growing crops. However, may injure certain crop plants slowing growth and development at application rates necessary to stunt or kill the weeds. Accordingly, some acetanilide herbicides such as metolachlor cannot be used for controlling weeds in the presence of certain crops. Obviously, a safening agent consisting of a composition that could be used to treat the seed of the crop plant, the crop plant locus or the crop plant itself, resulting in a reduction of injury due to application of the herbicide without a corresponding reduction of herbicidal action on the weed, would be quite beneficial.

DESCRIPTION OF THE INVENTION

In accordance with the novel aspects of the present invention, injury to sorghum, due to application thereto of metolachlor, may be reduced without a corresponding reduction to injury to the weeds by application to the crop plant locus or the seed of the crop plant prior to planting of an effective amount of a safening agent comprising a 2,4-disubstituted-5-thiazolecarboxylic acid or derivative thereof having the formula

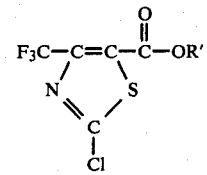

wherein R' is selected from the group consisting of hydrogen, agriculturally acceptable cations, alkyl (1–10 carbon atoms being preferred), phenyl, phenyl substituted by halogen (especially chlorine) and benzyl. The term "alkyl" is understood to include branched and unbranched groups.

The term "agriculturally acceptable cations" is understood to mean those cations that are commonly used to form the salt of the free acid. Such cations include, but are not limited to, alkali metal, alkaline earth, substituted amine and ammonium cations.

The amount of safening agent employed in the method and compositions of the invention will vary depending upon the particular rate of application of the herbicide, the crop species to be protected as well as the manner of application of the safening agent. In each instance, the amount employed is a safening effective amount, i.e., the amount which reduces crop injury by the herbicide.

The safening agent may be applied to the plant locus in a mixture with the herbicide, sequentially or it may be applied directly to the seed of the crop plant. By application to the "plant locus" is meant application to the plant growing medium, such as the soil, as well as the seeds, emerging seedlings, roots, stems, leaves, flowers, fruits or other plant parts.

Thus, one embodiment of the present invention relates to a method for selectively preventing the growth of weeds in the presence of sorghum plants which comprises applying to the sorghum plant locus a herbicidally effective amount of metolachlor, said sorghum plants having been germinated from seeds treated with a safening effective amount of the aforedescribed safening agent.

The amount of metolachlor employed is well within the skill of the art and is disclosed in U.S. pat. No. 3,937,730.

To illustrate the effectiveness of the thiazolecarboxylic acids and derivatives thereof, the following examples are presented. These examples are presented merely as being illustrative of the novel aspects of the invention and are not intended to be a limitation as to the scope thereof. It should be noted that the herbicide utilized in each of the Examples was DUAL herbicide manufactured by Ciba-Geigy Corporation. As noted previously, the active ingredient of DUAL is metolachlor.

EXAMPLE 1

A good grade of top soil is placed in a container and compacted to a depth of approximately 1.27 cm. from the top of said container. A predetermined number of sorghum, green foxtail, crabgrass and barnyardgrass seeds were applied to the soil surface. The seeds were then covered with top soil and the surface was treated with a mixture of metolachlor (formulated as DUAL) and safening agent. The plants are observed at the end of approximately 18 days and the results in terms of percent inhibition recorded. Table I summarizes the results of tests conducted in accordance with Example 1.

was placed on the pre-seeded pots. The soil surface was then treated with metolachlor (formulated as DUAL).

TABLE 1

| RATE OF HERBICIDE (kg/h) | SAFENING AGENT | RATE OF SAFENING AGENT (kg/h) | PERCENT INHIBITION | | | |
|---|---|---|---|---|---|---|
| | | | SORGHUM | GREEN FOXTAIL | CRAB GRASS | BARNYARD GRASS |
| — | Ethyl 2-chloro-4-trifluoro-methyl-5-thiazolecarboxylate | 0.14 | 0 | 0 | 0 | 0 |
| — | Ethyl 2-chloro-4-trifluoro-methyl-5-thiazolecarboxylate | 0.56 | 5 | 0 | 0 | 0 |
| — | Ethyl 2-chloro-4-trifluoro-methyl-5-thiazolecarboxylate | 2.24 | 15 | 0 | 0 | 0 |
| 0.14 | — | — | 13 | 97 | 97 | 98 |
| 0.56 | — | — | 60 | 98 | 99 | 99 |
| 2.24 | — | — | 84 | 99 | 100 | 100 |
| 0.14 | Ethyl 2-chloro-4-trifluoro-methyl-5-thiazolecarboxylate | 0.14 | 0 | 99 | 99 | 99 |
| 0.56 | Ethyl 2-chloro-4-trifluoro-methyl-5-thiazolecarboxylate | 0.14 | 0 | 99 | 99 | 99 |
| 2.24 | Ethyl 2-chloro-4-trifluoro-methyl-5-thiazolecarboxylate | 0.14 | 70 | 100 | 100 | 100 |
| 0.14 | Ethyl 2-chloro-trifluoro-methyl-5-thiazolecarboxylate | 0.56 | 8 | 98 | 97 | 98 |
| 0.56 | Ethyl 2-chloro-trifluoro-methyl-5-thiazolecarboxylate | 0.56 | 10 | 99 | 99 | 99 |
| 2.24 | Ethyl 2-chloro-trifluoro-methyl-5-thiazolecarboxylate | 0.56 | 15 | 100 | 100 | 100 |
| 0.14 | Ethyl 2-chloro-trifluoro-methyl-5-thiazolecarboxylate | 2.24 | 10 | 98 | 98 | 99 |
| 0.56 | Ethyl 2-chloro-trifluoro-methyl-5-thiazolecarboxylate | 2.24 | 10 | 100 | 99 | 100 |
| 2.24 | Ethyl 2-chloro-trifluoro-methyl-5-thiazolecarboxylate | 2.24 | 15 | 100 | 100 | 100 |

EXAMPLE 2

A predetermined number of sorghum seeds were placed on top of a good grade of top soil. The cover layer was then treated with an appropriate amount of safening agent. A cover layer of soil treated with the metolachlor (formulated as DUAL) was placed on top of the seeds. The plants were observed at the end of approximately 21 days and the results in terms of percent inhibition recorded. Table II summarizes the results of tests conducted in accordance with Example 2.

TABLE II

| RATE OF HERBICIDE (kg/h) | SAFENING AGENT | RATE OF SAFENING AGENT(kg/h) | PERCENT INHIBITION SORGHUM |
|---|---|---|---|
| — | Ethyl 2-chloro-4-trifluoro-methyl-5-thiazolecarboxylate | 8.96 | 0 |
| 0.56 | — | — | 50 |
| 4.48 | — | — | 97 |
| 0.56 | Ethyl 2-chloro-4-trifluoro-methyl-5-thiazolecarboxylate | 8.96 | 0 |
| 4.48 | | 8.96 | 75 |

As noted above, crop plants may be protected from herbicidal activity by treating the crop seed with the safening agent prior to planting. Example 3 illustrates such activity.

EXAMPLE 3

Sorghum seeds were treated with a solution of the appropriate safening agent in dichloromethane. The solvent was evaporated which left only the safening agent on the seed. Untreated and treated sorghum seeds were planted in pots. Selected weed species were planted in separate pots. 1.27 cm. deep soil cover layer Approximately 21 days later, the results were observed and recorded. Table III summarizes the results observed when tests were conducted in accordance with Example 3.

TABLE III

| RATE OF HERBICIDE (kg/h) | SAFENING AGENT | PERCENT SORGHUM INHIBITION SEED TREATMENT CONCENTRATION (GRAMS OF SAFENING AGENT/ KILOGRAMS OF SEED) | | | |
|---|---|---|---|---|---|
| | | 0 | 0.6 | 2.5 | 10 |
| — | Ethyl 2-chloro-4-trifluoromethyl-5-thiazolecarboxylate | 0 | 0 | 0 | 20 |
| 0.07 | Ethyl 2-chloro-4-trifluoromethy-5-thiazolecarboxylate | 0 | 0 | 0 | 23 |
| 0.14 | Ethyl 2 chloro-4-trifluoromethyl-5-thiazolecarboxylate | 5 | 0 | 0 | 15 |
| 0.28 | Ethyl 2-chloro-4-trifluoromethyl-5-thia- | 0 | 0 | 0 | 45 |

TABLE III-continued

| RATE OF HERBICIDE (kg/h) | SAFENING AGENT | PERCENT SORGHUM INHIBITION SEED TREATMENT CONCENTRATION (GRAMS OF SAFENING AGENT/ KILOGRAMS OF SEED) | | | |
| --- | --- | --- | --- | --- | --- |
| | | 0 | 0.6 | 2.5 | 10 |
| 0.56 | zolecarboxylate | 25 | 0 | 0 | 25 |
| 1.12 | Ethyl 2-chloro-4-tri-fluoromethyl-5-thia-zolecarboxylate | 40 | 5 | 0 | 35 |
| 2.24 | Ethyl 2-chloro-4-tri-fluoromethyl-5-thia-zolecarboxylate | 73 | 15 | 13 | 23 |

EXAMPLE 4

Two rows of sorghum and weed were seeded at 1.86 to 3.1 cm. depth in Ray silt loam soil. The soil is then treated with metolachlor (formulated as DUAL) and safening agent. Approximately 19 days later, the plants were observed and the results recorded. Table IV summarizes the results of tests conducted in accordance with Example 4.

TABLE IV

| RATE OF HERBICIDE (kg/h) | SAFENING AGENT | RATE (kg/h) | PERCENT INHIBITION | | | | | |
| --- | --- | --- | --- | --- | --- | --- | --- | --- |
| | | | SORGHUM | JIMSON WEED | MORNING GLORY | BARNYARD GRASS | PANICUM | FOXTAIL |
| 4.48 | — | — | 87 | 92 | 42 | 100 | 100 | 100 |
| 4.48 | Ethyl 2-chloro-4-trifluoro-methyl-5-thia-zolecarboxylate | 2.24 | 28 | 90 | 40 | 100 | 100 | 100 |

EXAMPLE 5

Sorghum seeds were treated with a solution of the appropriate safening agent in dichloromethane. The solvent was evaporated which left only the safening agent on the seed. Four rows of seed were planted for each treatment and metolachlor (formulated as DUAL) was applied to the soil surface as a pre-emergent. Table V summarizes the results observed when tests were conducted in accordance with Example 5.

TABLE V

| RATE OF HERBICIDE (kg/h) | SAFENING AGENT | PERCENT SORGHUM INHIBITION SEED TREATMENT CONCENTRATION (GRAMS OF SAFENING AGENT/ KILOGRAM OF SEED) | | | |
| --- | --- | --- | --- | --- | --- |
| | | 0 | 1.25 | 2.5 | 5 |
| — | Benzyl 2-chloro-4-trifluoromethly-5-thiazole carboxylate | 0 | 0 | 2 | 2 |
| 2.24 | Benzyl 2-chloro-4-trifluoromethyl-5-thiazole carboxylate | 58 | 0 | 0 | 0 |
| 4.48 | Benzyl 2-chloro-4-trifluoromethyl-5-thiazole carboxylate | 80 | 10 | 8 | 8 |

In Example 5 above, 100 percent control of pigweed, giant foxtail and purslane was observed.

The above examples illustrate that the thiazolecarboxylates of the present invention are useful in reducing herbicidal injury to sorghum crop plants. The safening agents may be applied to the plant locus as a mixture, i.e., a mixture of a herbicidally effective amount of herbicide and a safening effective amount of safening agent, or sequentially, i.e., the plant locus may be treated with an effective amount of the herbicide followed by a treatment with the safening agent or vice versa. The ratio of herbicide to safening agent may vary depending upon the crop species to be protected, weeds to be inhibited, etc., but normally a herbicide to safening agent ratio ranging from 1:25 to 25:1 (preferably 1:5 to 5:1) parts by weight may be employed.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form offinely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agun, dispersing agent, or emulsifying agent or any suitable combination of these.

When applying the herbicide, safening agent or mixture thereof to the plant locus, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, spreaders, power dusters, boom and hand sprayers, spray dusters and granular applications. The compositions can also be applied from airplanes as a dust or spray. If desired, application of the compositions of the invention to plants can be accomplished by incorporating the compositions in the soil or other media.

The above examples also illustrate a preferred embodiment of the invention, i.e. protecting the crop by treating the crop seed with an effective amount of safening agent prior to planting. In other words, a preferred embodiment of the present invention is the selective inhibition of weeds in the presence of sorghum plants by applying metolachlor to the sorghum plant locus, said sorghum plant being grown from seed treated with a safening effective amount of a safening agent described herein. Generally, small amounts of safening agent are required to treat such seeds. Tables 3 and 5 illustrate that a weight ratio of as little as 0.6 parts of safener per 1000 parts of seed may be effective. The amount of safener utilized in treating the seed may be increased if desired. Generally, however, a weight ratio of safening agent to seed weight may range from 0.1 to 10.0 parts of safening agent per 1000 parts of seed. The determination of the effective amount of safening agent required is well within the skill of the art.

Since only a very small amount of active safening agent is usually required for the seed treatment, the compound preferably is formulated as a powder or an emulsifiable concentrate which can be diluted with water by the seed treater for use in the seed treating apparatus. Of course, under certain conditions, it may be desirable to dissolve the safening agent in an organic solvent for use as a seed treatment or the pure compound alone may be used under properly controlled conditions.

There are thus also provided by this invention novel seed treating compositions containing one or more of the described active safening agents intimately dispersed in an inert carrier or diluent for the intended use. Such carriers may be either solids, such as talc, clay, diatomaceous earth, sawdust, calcium carbonate, and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active safening agent in liquids used as a carrier in which the agent is not completely soluble. Emulsifying agents and wetting agents are sold under numerous tradenames and may be either pure compounds, mixtures of compounds of the same general groups, or they may be mixtures of compounds of different classes. Typical satisfactory surface-active agents which may be used are alkali metal higher alkylarylsulfonates such as sodium dodecylbenzenesulfonate and the sodium salts of alkylnaphthalenesulfonic acids, fatty alcohol sulfates such as the sodium salts of monesters or sulfuric acid with n-aliphatic alcohols containing 8-18 carbon atoms, long chain quaternary ammonium compounds, sodium salts of petroleum-derived alkylsulfonic acids, polyethylene sorbitan monooleate, alkylaryl polyether alcohols, water-soluble lignin sulfonate salts, alkalicasein compositions, long chain alcohols usually containing 10-18 carbon atoms, and condensation products of ethylene oxide with fatty acids, alkylphenols and mercaptans.

PREPARATION OF THE SAFENING AGENTS

The thiazolecarboxylic acids and derivatives of the foregoing formula may be prepared by preparation of 2-oxo-2,3-dihydro-4-substituted-5-thiazolecarboxylates by reacting portions of β-aminoacrylates and chlorocarbonylsulfenyl chloride. Crystallization of the resulting mixture from hexane yields the appropriate 2-oxo-2,3-dihydro-4-substituted-5-thiazolecarboxylate which may be converted to the appropriate 2-chloro-4-substituted-5-thiazolecarboxylate by reaction with excess phosphorus oxychloride. Excess phosphorus oxychloride is removed under reduced pressure and the residue poured into ice water. Extraction with ether and washing with 5% sodium hydroxide results in the 2-chloro-4-substituted-5-thiazolecarboxylate. For purposes of clarification, this method is summarized by the following scheme:

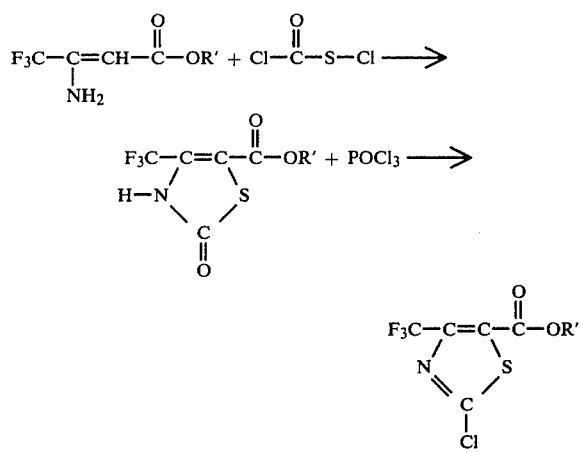

β-aminoacrylates may be prepared according to known procedures such as that specified in Lutz et al, *Journal of Heterocyclic Chemistry*, Volume 9, Page 513 (1972) or they may be prepared by mixing 0.5 moles of ethyl acetoacetate or methyl acetoacetate in 200 ml. of methanol and 100 ml. of saturated sodium acetate and passing through the appropriate nitrile for several hours. The reaction mixture is poured into ice wter and the organic layer extracted with ether. The ether solution is dried and concentrated and the residue distilled. A mixture of about 0.1 mole of said residue and 50 ml. of 30% ammonium hydroxide or sodium hydroxide is stirred for a long period. The reaction mixture is extracted with methylene chloride and the methylene chloride extracts dried and concentrated. Fractional distillation of the residue results in the β-aminoacrylate.

In order to more fully illustrate the manner in which the 2,4-disubstituted-5-thiazolecarboxylates of the present invention are prepared, the following examples are presented.

EXAMPLE 6

Preparation of Ethyl 2-Chloro-4-Trifluoromethyl-5-Thiazolecarboxylate. A mixture of 13.0 g (0.0992 mole) of chlorocarbonylsulfenyl chloride, 17 g (0.0928 mole) of ethyl 3-amino-4,4,4-trifluorocrotonate and 50 ml. of chlorobenzene was heated at 135° C. for 2 hours, cooled and triturated with 200 ml. of petroleum ether. The light yellow precipitate was recrystallized from hexane-ether to give 12.2 g (55%) of white prisms, m.p.

121°–123° C., which was identified as ethyl 2,3-dihydro-2-oxo-4-trifluoromethyl-5-thiazolecarboxylate. A mixture of 10 g (0.0415 mole) of ethyl 2,3-dihydro-2-oxo-4-trifluoromethyl-5-thiazolecarboxylate, 30 ml. of $POCl_3$ and 1 ml. of dimethylformamide was held at reflux for 87 hours. The reaction mixture was poured into 500 ml. of ice water and extracted three times with 60 ml. of ether. The ether solution was washed with saturated sodium chloride solution, dried ($MgSO_4$) and concentrated under reduced pressure to give 10.2 g of light yellow solid, m.p. 57°–60° C., which was recrystallized from hexane to give 9.95 g (92.4%) of ethyl 2-chloro-4-trifluoromethyl-5-thiazolecarboxylate as light yellow solid, m.p. 58°–59° C.

Anal. Calc'd for $C_7H_5F_3ClNO_2S$: C, 32.38; H, 1.94; N, 5.40. Found: C, 32.33; H, 1.98; N, 5.35.

Various esters may be prepared by reacting the compound of Example 6 with sodium hydroxide to form the free acid and then forming the acid chloride by reaction with thionyl chloride. Reaction of the acid chloride with an alcohol results in the desired ester.

EXAMPLE 7

Preparation of 2-Chloro-4-Trifluoromethyl-5-Thiazolecarboxylic Acid. A mixture of 116 g (0.4468 mole) of ethyl 2-chloro-4-trifluoromethyl-5-thiazolecarboxylate, 18 g (0.45 mole) of sodium hydroxide, 200 ml. of water, 400 ml. of tetrahydrofuran was stirred at room temperature for 16 hours and made acidic with 50 ml. of concentrated hydrochloric acid. The reaction mixture was extracted twice with 200 ml. of ether. The ether-tetrahydrofuran solution was dired ($MgSO_4$) and concentrated under reduced pressure. The residual oil was treated with benzene and the benzene solution was concentrated under reduced pressure to remove the last trace of water. The residual solid was recrystallized from hexane-benzene to give 76 g (73.4%) of 2-chloro-4-trifluoromethyl-5-thiazolecarboxylic acid, m.p. 131°–131.5° C.

Anal. Calc'd for $C_5H_1ClF_3NO_2S$: C, 25.92; H, 0.47; Cl, 15.31; N, 6.05.

Found: C, 26,07; H, 0.52; Cl, 15.64; N, 6.10.

EXAMPLE 8

Preparation of 2-Chloro-4-Trifluoromethyl-5-Thiazolecarboxylic Acid Chloride. A mixture of 36.0 g (0.1554 mole) of the acid of Example 7 and 171 g (1.437 mole) of thionyl chloride were held at reflux for 6 hours. Excess thionyl chloride was removed under reduced pressure and the residue (38.1 g, 98%) was reacted as described in Examples 9–14.

EXAMPLE 9

Preparation of Isopropyl 2-Chloro-4-Trifluoromethyl-5-Thiazolecarboxylate. The acid chloride of Example 8 (5.2 g), and 10 g of isopropanol were held at reflux for 16 hours. Excess alcohol was removed under reduced pressure. The residue was dissolved in 50 ml. of ether. The ether solution was washed with sodium bicarbonate, dried ($MgSO_4$) and concentrated under reduced pressure. The crude product was distilled at 1 mm. on a Kugelrohr to give 4.9 g (86%) of the desired product as colorless liquid, $n_D^{25}=1.4655$.

Anal. Calc'd. for $C_8H_7ClF_3NO_2S$: C, 35.10; H, 2.58; N, 5.12; Cl, 12.96. Found: C, 35.15; H, 2.62; N. 5.11; Cl, 12.90.

EXAMPLE 10

Preparation of Benzyl 2-Chloro-4-Trifluoromethyl-5-Thiazolecarboxylate. The procedure of Example 9 was repeated utilizing benzyl alcohol in lieu of isopropanol.

Anal. Calc'd. for $C_{12}H_7ClF_3NO_2S$: C, 44,80; H, 2.19; N, 4.35; Cl, 11.02. Found: C, 44.86; H, 2.19; N, 4.34; Cl1, 11.09.

EXAMPLES 11–16

Utilizing the appropriate alcohol and the procedure of Example 9, the following compounds have been prepared.

n-Butyl 2-Chloro-4-Trifluoromethyl-5-Thiazolecarboxylate, $n_D^{25}=1.4685$.

Anal. Calc'd. for $C_9H_9ClF_3NO_2S$: C, 37.57; H, 3.15; N, 4.87. Found: C, 37.54; H, 3.17; N, 4.90.

n-Hexyl 2-Chloro-4-Trifluoromethyl-5-Thiazolecarboxylate, $n_D^{25}=1.4657$.

Anal. Calc'd. for $C_{11}H_{13}Cl F_3NO_2S$: C, 41.84; H, 4.15; N. 4.44. Found: C, 41.86; H, 4.15; N. 4.43.

n-Octyl 2-Chloro-4-Trifluoromethyl-5-Thiazolecarboxylate, $n_D^{25}=1.4658$.

Anal. Calc'd. for $C_{13}H_{17}Cl F_3NO_2S$: C, 45.42; H, 4.98; N, 4.07. Found: C, 45.58; H, 5.05; N, 4.04.

Methyl 2-Chloro-4-Trifluoromethyl-5-Thiazolecarboxylate. The residue was crystallized at low temperature from hexane to give 3.25 g (95%) of methyl 2-chloro-4-tri-fluoromethyl-5-thiazolecarboxylate as light yellow prisms, m.p. 32°–34° C.

Anal. Calc'd. for $C_6H_3F_3NO_3S$: C, 31.72; H, 1.77; N, 6.17. Found: C, 31.88; H, 1.80; N, 6.20.

Salts may be prepared by reaction of the free acid with the appropriate based.

Phenyl 2-Chloro-4-Trifluoromethyl-5-Thiazolecarboxylate, $n_D^{25}=1.5389$.

Anal. Calc'd. for $C_{11}H_5Cl F_3NO_2S$: C, 42.94; H, 1.64; N, 4.55. Found: C, 42.97; H, 1.67; N, 4.58.

p-Chlorophenyl 2-Chloro-4-Trifluoromethyl-5-Thiazolecarboxylate, $n_D^{25}=1.5552$.

Anal. Calc'd. for $C_{11}H_4Cl_2F_3NO_2S$: C, 38.60; H, 1.17; N, 4.09. Found: C, 39.08; H, 1.00; N, 4.09.

EXAMPLE 17

Preparation of Sodium Salt of 2-Chloro-4-Trifluoromethyl-5-Thiazolecarboxylic Acid, Monohydrate. A mixture of 116 g (0.4468 mole) of ethyl 2-chloro-4-trifluoromethyl-5-thiazolecarboxylate, 18 g (0.45 mole) of sodium hydroxide, 200 ml. of water and 400 ml. of tetrahydrofuran was stirred at room temperature for 16 hours. The aqueous solution was concentrated and dried under vacuum to give the sodium salt of 2-chloro-4-trifluoromethyl-5-thiazolecarboxylate, monohydrate as a white solid, m.p. 211°–215° C.

Anal. Calc'd. for $C_5H_2Cl F_3NO_3S$: C, 22.10; H, 0.74; N, 5.16. Found: C, 22.14; H, 0.71; N, 5.21.

EXAMPLE 18

Preparation of Triethanolamine Salt of 2-Chloro-4-Trifluoromethyl-5-Thiazolecarboxylic Acid. To a cold (5° C.) solution of 6.93 g (0.03 mole) of 2-chloro-4-trifluoromethyl-5-thiazolecarboxylic acid in 20 ml. of ether was added 4.47 g (0.03 mole) of triethanolamine. The reaction mixture was stirred at room temperature for 18 hours and filtered to give 8.78 g (77%) of the desired product, m.p. 101°–102° C.

Aanl. Calc'd, for $C_{11}H_{16}Cl F_3N_2O_5S$: C, 34.69; H, 4.23; N, 7.36. Found: C, 34.89; H, 4.07; N, 7.39.

EXAMPLE 19

Preparation of Isopropylamine Salt of 2-Chloro-4-Trifluoromethyl-5-Thiazolecarboxylic Acid. To a cold (6° C.) solution of 4.55 g (0.0196 mole) of the free acid in 20 ml. of ether was added dropwise a solution of 1.16 g (0.0196 mole) of isopropylamine in 10 ml. of ether. The reaction mixture was stirred at room temperature for 1 hour and the white precipitate was filtered to give 5.50 g (96.5%) of the desired product, m.p. 132°–134° C.

Anal. Calc'd. for $C_8H_{10}Cl\ F_3N_2O_2S$: C, 33.05; H, 3.47; N, 9.64. Found: C, 33,47; H, 3.55; N, 9.72.

EXAMPLE 20

Preparation of Diethylamine Salt of 2-Chloro-4-Trifluoromethyl-5-Thiazolecarboxylic Acid. To a cold (6° C.) solution of 6.93 g (0.03 mole) of the free acid in 20 ml. of ether was added 2.19 g (0.03 mole) of diethylamine in 100 ml. of ether. The precipitate, which formed immediately, was filtered to give 7.95 g (86.4%) of the desired product, m.p. 131°–132° C.

Anal. Calc'd for $C_9H_{12}Cl\ F_3N_2O_2S$: C, 35.47; H, 3.97; N, 9.20. Found: C, 35.60; H, 3.97; N, 9.21.

In accordance with the novel aspects of the present invention, the thiazolecarboxylates have been found to be effective in reducing herbicidal injury to sorghum plants due to application of metolachlor. The safening agents most preferred are the alkyl, especially ethyl, and benzyl esters of 2-chloro-4-trifluoromethyl-5-thiazolecarboxylic acid.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method for selectively preventing the growth of weeds in the presence of sorghum plants with comprises applying to the sorghum plant locus a herbicidally effective amount of 2-chloro-N-(2-methoxy-1-methylethyl)-6'-ethyl-o-acetotoluidide having the formula

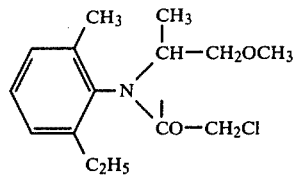

said sorghum plants having been germinated from seeds treated with a safening effective amount of a compound of the formula wherein R' is selected from the group consisting of alkyl having up to 10 carbon atoms and benzyl.

2. A method according to claim 1 wherein R' is ethyl.
3. A method according to claim 1 wherein R' is benzyl.
4. A method for safening sorghum from the herbicidal effects of 2-chloro-N-(2-methoxy-1-methylethyl)-6'-ethyl-o-acetotoluidide having the formula which comprises applying to the sorghum plant locus a safening effective amount of a compound having the formula wherein R' is selected from the group consisting of alkyl having up to 10 carbon atoms and benzyl.

5. A method according to claim 4 wherein R' is ethyl.
6. A method according to claim 4 wherein R' is benzyl.

* * * * *

UNITED STATES PATENT AND TRADEMARK OFFICE
CERTIFICATE OF CORRECTION

PATENT NO. : 4,251,261

DATED : Feb. 17, 1981

INVENTOR(S) : Robert K. Howe, Bridgeton; Len F. Lee, Maryland Hts., both of Mo.

It is certified that error appears in the above—identified patent and that said Letters Patent are hereby corrected as shown below:

Column 6, line 22, delete "offinely-divided" and insert --of finely-divided--.

Column 6, line 26, delete "agun" and insert --agent--.

Column 1, replace formula

"
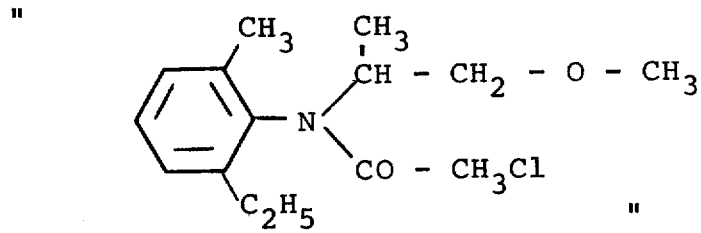
"

UNITED STATES PATENT AND TRADEMARK OFFICE
CERTIFICATE OF CORRECTION

PATENT NO. : 4,251,261  
DATED : Feb. 17, 1981  
INVENTOR(S) : Robert K. Howe, Bridgeton; Len F. Lee, Maryland Hts., both of Mo.

It is certified that error appears in the above-identified patent and that said Letters Patent are hereby corrected as shown below:

(Column 1, continued)

and insert

-- 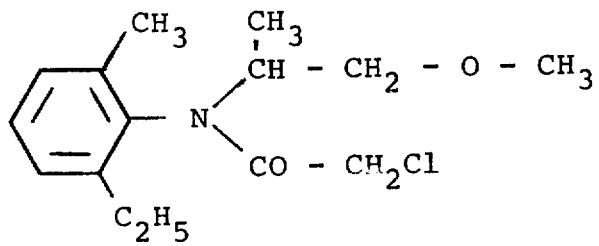 --.

Signed and Sealed this

Twenty-ninth Day of November 1983

[SEAL]

Attest:

GERALD J. MOSSINGHOFF

Attesting Officer    Commissioner of Patents and Trademarks